US00PP36653P2

(12) United States Plant Patent
Boxriker

(10) Patent No.: US PP36,653 P2
(45) Date of Patent: May 6, 2025

(54) ***DIANTHUS* PLANT NAMED 'KLEDP23440'**

(50) Latin Name: ***Dianthus caryophyllus* L.**
Varietal Denomination: KLEDP23440

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/671,979

(22) Filed: May 22, 2024

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./272, 273
CPC ..... A01H 5/02
See application file for complete search history.

(56) References Cited

PUBLICATIONS

Selecta *Dianthus* Early Spring Crops Catalog 2023/2024; 2023; 79 pages.*
www.bfgsupply.com/media/9050/2024-pacific-plug-product-program.pdf; 2024; 7 pages.*
https://www.ballseed.com/webtrackplantinfo.aspx?phid=022508412051944; Aug. 22, 2024; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new *Dianthus* plant designated 'KLEDP23440' particularly distinguished by white and purple flowers, good earliness, and upright plant with long flower stems, is disclosed.

1 Drawing Sheet

Genus and species: *Dianthus caryophyllus* L.
Variety denomination: 'KLEDP23440'.

BACKGROUND OF THE NEW PLANT

The present invention comprises a new and distinct variety of *Dianthus*, botanically known as *Dianthus caryophyllus* L. and hereinafter referred to by the variety name 'KLEDP23440'. 'KLEDP23440' originated from an open pollination conducted in 2017 in Stuttgart, Germany between the proprietary *Dianthus* female parent 'KLEDP16194' (unpatented) and an unknown male. The seeds from this cross were sown in Stuttgart, Germany and a single plant was selected in May 2018.

In August 2018, 'KLEDP23440' was first vegetatively propagated by vegetative stem cuttings in Stuttgart, Germany. 'KLEDP23440' was found to reproduce true to type in successive generations of asexual propagation in Stuttgart, Germany via vegetative cuttings.

SUMMARY

The following are the most outstanding and distinguishing characteristics of 'KLEDP23440' when grown under normal horticultural practices in Stuttgart, Germany.

1. White and purple flowers;
2. Good earliness; and
3. Upright plant with long flower stems.

DESCRIPTION OF THE PHOTOGRAPH

This new *Dianthus* plant is illustrated by the accompanying photograph of a 14-week-old plant taken in May 2022 and grown in a greenhouse in Stuttgart, Germany. The colors shown are as true as can be reasonably obtained by conventional photographic procedures. The photograph is a whole plant photograph of 'KLEDP23440' and shows the foliage, buds, and flowers.

DESCRIPTION

The following detailed descriptions set forth the distinctive characteristics of 'KLEDP23440'. The data which define these characteristics were collected from asexual reproductions carried out in Stuttgart, Germany. Data was collected in May 2024 from plants planted in September 2023 that were 23 weeks old and grown in a greenhouse. Color references are to The R.H.S. Colour Chart of The Royal Horticultural Society of London (R.H.S.), 5$^{th}$ edition (2007).

Classification:
- *Family.*—Caryophyllaceae.
- *Botanical.*—*Dianthus caryophyllus* L.
- *Designation.*—'KLEDP23440'.
- *Type.*—Pot carnation.

Parentage:
- *Female parent.*—*Dianthus* 'KLEDP16194' (unpatented).
- *Male parent.*—Unknown.

Plant:
- *Propagation type.*—Vegetative cuttings.
- *Time to produce a rooted young plant.*—28 days.
- *Root description.*—Fine roots, RHS 155C.
- *Rooting habit shape.*—Lanceolate.
- *Plant form.*—Upright.
- *Plant height.*—24.0 cm.
- *Plant diameter or spread.*—39.0 cm.

Lateral branches/stems:
*Shape of the branch in cross-section*.—Circular.
*Hollowness of the branch*.—Absent.
*Length*.—26 cm.
*Diameter*.—0.3 cm.
*Stem thickness*.—Thick.
*Internode length*.—5.6 cm.
*Internode quantity per branch*.—5.
*Number of internodes per branch/stem*.—5.
*Node length*.—0.5 cm.
*Node diameter*.—0.5 cm.
*Texture*.—Smooth.
*Color*.—RHS 137A.
*Flower clustering on the lateral branch*.—None.

Foliage:
*Arrangement*.—Opposite.
*Length*.—6.1 cm.
*Width*.—0.5 cm.
*Shape*.—Obovate.
*Apex*.—Acute.
*Base*.—Obtuse.
*Margin*.—Entire.
*Texture* (*both upper and lower surfaces*).—Smooth.
*Cross-section of the leaf*.—Moderately concave.
*Curvature of the leaf*.—Absent.
*Glaucosity of the leaf*.—Weak.
*Leaf color* (*both immature and mature*).—Immature: Upper surface: RHS N137C. Lower surface: RHS N137A. Mature: Upper surface: RHS N137A. Lower surface: RHS 137A.
*Venation pattern*.—Absent.

Flowers:
*Flower type and habit*.—Double flower.
*Fragrance*.—Present, sweet and fresh.
*Position of the flowers compared to the foliage of the plant*.—Far above.
*Profile of both the upper and lower part in the lateral view*.—Convex.
*Diameter of the flower*.—4.9 cm.
*Natural flowering season*.—Spring to autumn.
*Number of flowers per spray*.—1.
*Flower longevity on the plant*.—14 days.

Buds:
*Length*.—1.9 cm.
*Diameter*.—0.9 cm.
*Shape*.—oblong.
*Color*.—RHS 137C.
*Extrusion of the styles at the bud stage*.—Absent.

Corolla:
*Quantity of petals and arrangement*.—25 and arranged in 4 whorls.
*Corolla height*.—2.0 cm.
*Petal length*.—3.7 cm.
*Petal width*.—2.0 cm.
*Petal shape*.—Obtuse.
*Petal apex*.—Obtuse.
*Petal base*.—Acute.
*Petal margin*.—Crenate.
*Depth of petal margin*.—Shallow.
*Petal texture* (*both upper and lower surfaces*).—Smooth.
*Petal color*.—Immature: Upper surface: RHS NN155C with N79B macule and N78B flush. Lower surface: RHS NN155C. Mature: Upper surface: RHS NN155C with N79B macule and N78B flush. Lower surface: RHS NN155C.
*Macule*.—Present. Color: RHS N79B. Size (length): 0.3 cm.

Calyx:
*Quantity of sepals and arrangement*.—Composed of 6 sepals.
*Longitudinal axis of the lobes of the calyx*.—Straight.
*Shape*.—Acute.
*Calyx height*.—2.0 cm.
*Calyx diameter* (*at the apex*).—1.3 cm.
*Sepal texture* (*both upper and lower surfaces*).—Smooth.
*Sepal color*.—Upper surface: RHS 147B. Lower surface: RHS 147C.
*Position of the outer lobes of the epicalyx in relation to the calyx*.—Free.
*Apex shape of the outer lobes of the epicalyx*.—Acute.
*Tip length of the outer lobes of the epicalyx*.—0.3 cm.
*Apex shape of the inner lobes of the epicalyx*.—Short acuminate.
*Tip length of the inner lobes of the epicalyx*.—0.3 cm.

Peduncles:
*Length*.—1.5 cm.
*Diameter*.—0.2 cm.
*Strength*.—Medium.
*Texture*.—Smooth.
*Color*.—RHS 137A.

Reproductive organs:
*Stamens*.—Quantity per flower: 7. Filament length: 2.3 cm. Filament color: 157C RHS. Anther length: 0.1 cm. Anther diameter: Less than 0.1 cm. Anther color: RHS 199C. Pollen amount: None observed.
*Pistils*.—Quantity per flower: 2. Length: 1.0 cm. Diameter: 0.1 cm. Stigma: Color: RHS 155C. Shape: Filamentous. Length: 0.1 cm. Diameter: 0.1 cm. Style: Color: RHS 155C. Length: 0.1 cm. Diameter: 0.1 cm. Number of styles: 2. Shoulder: Absent. Ovary: Color: RHS 145D. Width: 0.2 cm. Texture: Smooth.

Seeds: None observed to date.

Disease and insect resistance: No particular disease or insect resistance observed.

COMPARISON OF 'KLEDP23440' WITH PARENTAL LINE AND KNOWN VARIETY

'KLEDP23440' is distinguished from the female parent as described in Table 1.

TABLE 1

Comparison with Parental Line

| Characteristic | 'KLEDP23440' | Female parent |
|---|---|---|
| Flower color | White and purple | White and red bicolor |
| Earliness | Early | Medium early |

'KLEDP23440' can be compared to the commercial *Dianthus* variety 'KLEDP23480' (U.S. Plant Pat. No. 36,216). Differences between the varieties are described in Table 2.

TABLE 2

Comparison with Similar Variety

| Characteristic | 'KLEDP23440' | 'KLEDP23480' |
|---|---|---|
| Flower color | White and purple | White and magenta |
| Earliness | Early | Very early |
| Habit | Upright with long flower stems | Upright with shorter flower stems |

I claim:

1. A new and distinct cultivar of *Dianthus* Plant Named 'KLEDP23440' as illustrated and described herein.

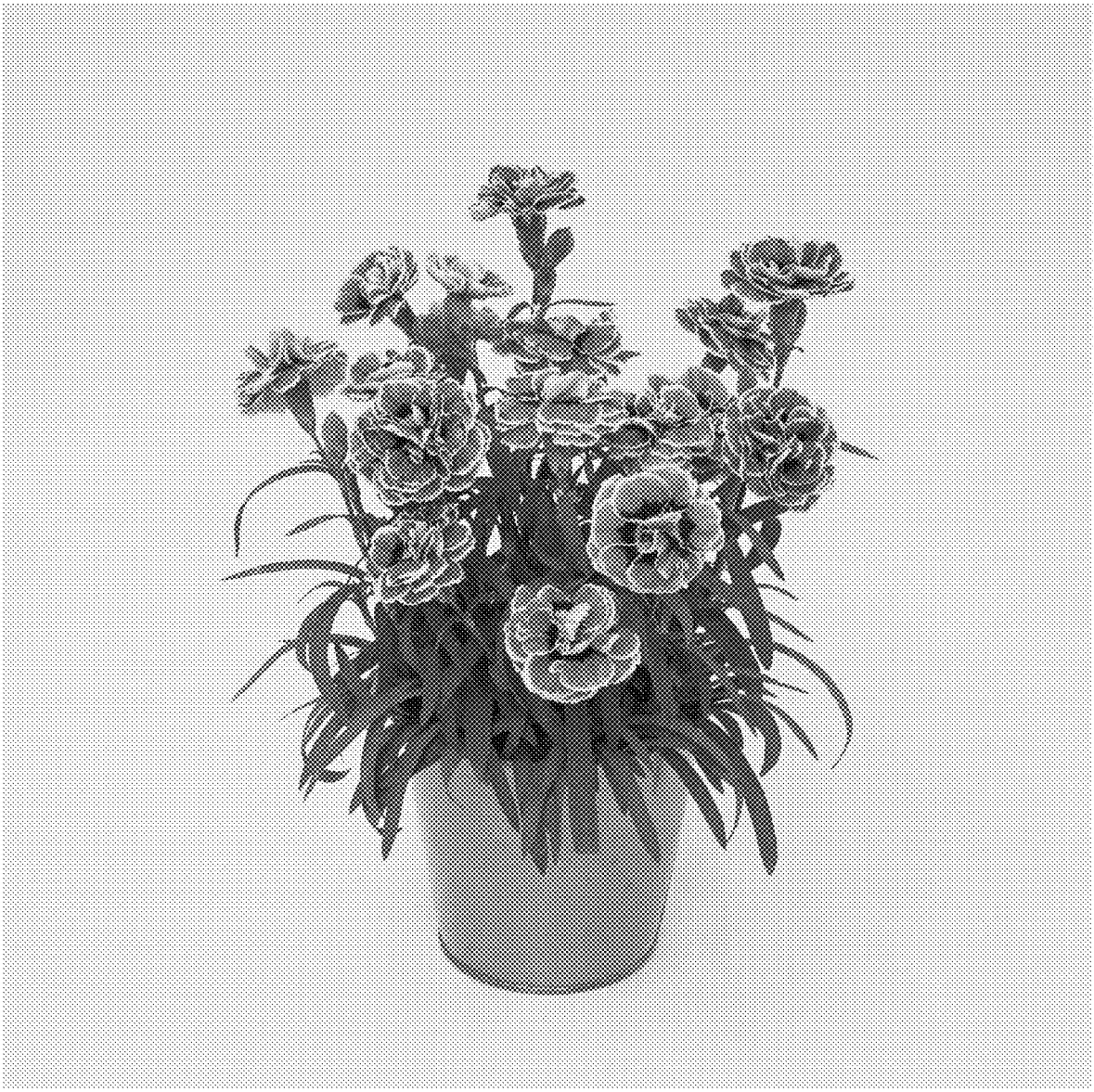

* * * * *